United States Patent
Bischoff et al.

(10) Patent No.: US 8,491,576 B2
(45) Date of Patent: Jul. 23, 2013

(54) LASER SYSTEM

(75) Inventors: Mark Bischoff, Jena (DE); Manfred Dick, Gefell (DE)

(73) Assignee: Carl Zeiss Meditec AG, Jena (DE)

( * ) Notice: Subject to any disclaimer, the term of this patent is extended or adjusted under 35 U.S.C. 154(b) by 423 days.

(21) Appl. No.: 12/671,279

(22) PCT Filed: Jul. 25, 2008

(86) PCT No.: PCT/EP2008/006140
§ 371 (c)(1),
(2), (4) Date: Jun. 29, 2010

(87) PCT Pub. No.: WO2009/015836
PCT Pub. Date: Feb. 5, 2009

(65) Prior Publication Data
US 2010/0274232 A1  Oct. 28, 2010

(30) Foreign Application Priority Data
Jul. 31, 2007  (DE) .......................... 10 2007 035 850

(51) Int. Cl.
*A61B 18/18* (2006.01)
*A61B 3/00* (2006.01)

(52) U.S. Cl.
USPC ....... 606/4; 606/5; 606/11; 351/200; 351/246

(58) Field of Classification Search
USPC .............................................. 606/4, 5, 10–12
See application file for complete search history.

(56) References Cited

U.S. PATENT DOCUMENTS

| 4,732,148 | A | * | 3/1988 | L'Esperance, Jr. | 606/5 |
| 4,887,592 | A | | 12/1989 | Loertscher | |
| 4,941,093 | A | | 7/1990 | Marshall et al. | |
| 5,102,409 | A | | 4/1992 | Balgorod | |
| 5,620,437 | A | | 4/1997 | Sumiya | |
| 2002/0111606 | A1 | | 8/2002 | Lemberg | |
| 2003/0069566 | A1 | | 4/2003 | Williams et al. | |
| 2004/0135971 | A1 | * | 7/2004 | Ulbers | 351/221 |
| 2004/0196432 | A1 | * | 10/2004 | Su et al. | 351/206 |
| 2004/0199149 | A1 | * | 10/2004 | Myers et al. | 606/4 |
| 2008/0051773 | A1 | * | 2/2008 | Ivanov et al. | 606/12 |
| 2008/0300581 | A1 | * | 12/2008 | Wiechmann et al. | 606/4 |

FOREIGN PATENT DOCUMENTS

| DE | 102006015051 A1 | 10/2006 |
| EP | 224322 A1 | 6/1987 |

(Continued)

OTHER PUBLICATIONS

German Search Report, dated May 30, 2008, issued in German Patent Application No. 10 2007 035 850.6.

(Continued)

*Primary Examiner* — Dawayne A Pinkney
(74) *Attorney, Agent, or Firm* — Leydig, Voit & Mayer, Ltd.

(57) ABSTRACT

A laser system for the irradiation of an eye includes a laser configured to emit a laser beam; a focusing device configured to focus the laser beam; and a beam-shaping device configured to generate a predetermined intensity distribution in a cross section of the laser beam such that an intensity minimum of the laser beam is disposed in region of a center of the cross section of the laser beam.

10 Claims, 4 Drawing Sheets

FOREIGN PATENT DOCUMENTS

| EP | 0257836 | A1 | 3/1988 |
| EP | 0467775 | A1 | 1/1992 |
| EP | 0525902 | A1 | 2/1993 |
| JP | 07265349 | A | 10/1995 |
| WO | 9325166 | A1 | 12/1993 |

OTHER PUBLICATIONS

International Search Report, mail date Nov. 20, 2008, issued in International Patent Application No. PCT/EP2008/006140.

* cited by examiner

LASER SYSTEM

This is a U.S. National Phase Application under 35 U.S.C. §371 of International Application No. PCT/EP2008/006140, filed on Jul. 25, 2008 and claims benefit to German Patent Application No. DE 10 2007 035 850.6, filed on Jul. 31, 2007. The International Application was published in German on Feb. 5, 2009 as WO 2009/015836 under PCT article 21 (2).

The invention relates to a laser system for the irradiation of an eye.

BACKGROUND

DE 102006015 051 describes a laser device for the treatment of the eye. Sensitive regions of the eye are irradiated in this process.

The applied laser radiation can pose a risk to the retina and especially to the macula. Pertinent standards, for instance, IEC 60825-1, provide reliable threshold values for the irradiation of the retina. The maximum permissible exposure values (MPE values) are threshold values pertaining to a safe radiation strength (watts per square centimeter) or radiation (joules per square centimeter). These values are stipulated separately for the skin and eyes. Such values are reference values that have been ascertained experimentally. Irradiation of the retina, especially of the macula—the site of the sharpest vision or of the optic nerve head—should be kept to a minimum since these are particularly sensitive places of the fundus of the eye. Laser radiation in the visible and near-infrared spectra (wavelength of about 400 nm to 1400 nm) penetrates virtually without diminishing all the way to the retina and can damage the very sensitive macula or else the pupil or the optic nerve head. When laser radiation is employed, the maximum permissible exposure values are always complied with everywhere on the fundus of the eye. If an anterior segment of an eye is exposed to a laser beam, radiation usually reaches the fundus of the eye as well. Even if an optical breakdown is achieved in the focus of the laser radiation for purposes of processing the tissue located there, laser radiation that was not absorbed still reaches the fundus of the eye and thus also particularly sensitive regions of the retina.

SUMMARY OF THE INVENTION

An aspect of the present invention is to provide a laser system that makes it possible to minimize the irradiation of sensitive regions of the eye when it is exposed to radiation.

In an embodiment a laser system for the irradiation of an eye, comprising a laser to emit a laser beam, a focusing device to focus the laser beam and a beam-shaping device for generating a predetermined intensity distribution in the cross section of the laser beam in such a way that the intensity minimum of the laser beam is located approximately in the center of the cross section of the laser beam, and the objective is also achieved by a method for treating an eye, in which a laser system having a beam-shaping device is employed. As a result, it is possible to carry out laser processing in an anterior or central segment of the eye in a way that significantly reduces damage to the retina and to the sensory elements located there. A high degree of radiation safety for particularly sensitive areas of the fundus of the eye, especially of the macula and of the optic nerve head, can be achieved by employing focused laser radiation in the anterior or central segment of the eye including the cornea, the lens and the vitreous body. Preferably, the beam bundle that propagates beyond the focus corresponds approximately to the input bundle.

An eye is primarily a sensory organ for the perception of electromagnetic radiation. Primarily, the eye is a sensory organ for the perception of light. In particular, the eye is a sensory organ for the image-forming perception of electromagnetic radiation. Primarily, the eye is a sensory organ of an animal, in particular a sensory organ of a human being.

Preferably, a laser comprises a radiation source that generates the radiation through induced emission. The radiation preferably comprises infrared radiation, especially preferably visible light or ultraviolet radiation. Preferably, the radiation source can emit laser radiation having wavelengths at which the eye has a high transmission, that is to say, the radiation can penetrate well all the way to the retina. Preferably, the radiation has wavelengths between 300 nm and 1400 nm, especially preferably wavelengths between 400 nm and 1200 nm. Preference is given to the use of continuously emitting, especially preferably clocked or pulsed lasers. These continuously emitting lasers or clocked continuous lasers preferably make use of powers ranging from 10 mW to 2.5 W, especially preferably powers ranging from 100 mW to 1.2 W. Preferably, focus diameters ranging from approximately 10 µm to a few millimeters, especially preferably from 50 µm to 300 µm, are employed. In the case of a clocked laser emission, laser radiation is preferably emitted over a time span between 1 ms and 10 ms. In the case of a pulsed laser emission, laser radiation is preferably emitted over a time span that is shorter than 1 ms. Preferably, lasers with pulse durations in the ms range, or in the ns or ps range are used, especially preferably lasers with pulse durations in the fs range are used. For the treatment of secondary cataracts on the lens, preferably a Q-switched Nd:YAG laser with pulse durations of preferably about 1 ns to 5 ns and pulse energies of preferably 1 mJ to 10 mJ is employed. When it comes to refractive surgery of the cornea or lens, preferably a femtosecond laser with pulse durations of preferably about 10 fs to 1 ps, preferably 100 fs to 300 fs, is used.

In this context, these femtosecond lasers preferably employ pulse energies ranging from a few nJ to about 10 µJ, especially preferably from 100 nJ to 2 µJ. The repetition rates of these ultrashort pulses are preferably from 1 kHz to 100 MHz. Special preference is given to repetition rates ranging from 50 kHz to 500 kHz.

A preferred use of pulsed lasers in the ns, ps or fs ranges is the operating principle of laser disruption. In this process, intensities $>10^8$ W/cm$^2$ that can lead to a brief formation of a plasma are generated in the region of focus at diameters preferably in the range from 1 µm to 20 µm. Experiments have shown that the energy consumption within the plasma does not amount to 100% and that at least 30% of the energy input continues to propagate behind this focus/plasma as well. Preferably, a safety diaphragm is employed in such an application case.

Preference is given to the use of argon lasers, diode lasers, diode-pumped solid state lasers, diode-pumped semiconductor lasers, frequency-doubled Nd:YAG lasers, etc. The lasers can be used as pulsed lasers or as continuous wave (CW) lasers. Moreover, other sources of light are also conceivable such as, for example, the focused light of a xenon lamp, light-emitting diodes (LEDs), superluminescent diodes (SLDs), etc. Preferably, laser systems, particularly preferably multi-length systems, are employed that are configured to emit waves in the green, yellow, red and/or infrared wavelengths. Preference is given to the use of fs laser systems for the treatment of the cornea, especially preferably for the treatment of the lens of the eye or of other elements of the anterior segment of the eye.

A laser beam is a beam that is emitted by a laser.

Preferably, the focusing device is a device that is suitable to focus the laser beam. Especially preferably, the focusing device comprises a lens. This makes it possible to focus the laser beam in a simple manner. The laser beam is preferably focused by means of an optical system, preferably by lens optics or mirror optics, or by diffractive or refractive micro-optics. Preferably, a contact lens that is placed onto the cornea performs part of the focusing. Preferably, a contact lens compensates for the refractive power of the cornea.

A beam-shaping device is preferably a device for structuring a cross section of the laser beam. Especially preferably, the beam-shaping device is configured to set an intensity distribution in a cross section of a laser beam. Preferably, the beam-shaping device is configured to perform geometrical beam shaping. Especially preferably, the beam-shaping device is configured to provide an area in which the laser radiation is present, and an area in which no laser radiation is present.

Preferably, the beam-shaping device comprises a diffractive optical element. Diffractive optical elements are preferably optical elements that serve to shape a laser beam. In this context, use is preferably made of the physical principle of diffraction of the laser beam on an optical grating. Preferably, the diffractive optical elements are glass substrates onto which the microstructures have been applied. Preferably, the microstructures were applied onto the glass substrates by means of photolithography. The use of a diffractive element allows beam shaping over the cross section of the laser beam without perceptible losses of laser energy having to be accepted, which is the case, for instance, with conventional diaphragm techniques.

Preferably, the beam-shaping device comprises a refractive optical element. Refractive optical elements are preferably elements that give rise to optical diffraction. Diffraction is preferably a change in the direction of a wave due to a local change in its propagation speed. The use of a refractive element can likewise allow beam shaping over the cross section of the laser beam without perceptible losses of laser energy having to be accepted, which is the case, for instance, with conventional diaphragm techniques.

Preferably, the beam-shaping device comprises digitally actuatable transmissive liquid-crystal optics. Preferably, liquid-crystal optics encompass a liquid crystal. A liquid crystal is preferably a substance that exhibits the properties of a liquid as well as those of a crystal.

With a transmissive liquid-crystal optics, the beam profile can be shaped dynamically without additional beam deflection. This is very advantageous in the case of variable processing locations in the anterior segment of the eye using, for instance, a scanner system, in order to quickly establish a suitable beam shape that is based on the current focal position and that keeps the residual radiation away from the macula. Since the geometry of the eye is previously known or can be measured individually, a beam profile is associated with each focal position in a cross section that protects, for example, the macula, from residual radiation. Thus, the liquid-crystal optics can be actuated in a targeted manner as a function of the xyz scanner position (focal position). In order to keep the energy density in the focus constant so that the quality of the therapy remains constant, the design of the beam profile cross section is preferably such that a constant transmission is established over the cross section of the transmissive liquid-crystal optics or of another dynamic beam-shaping element.

Preferably, the beam-shaping device comprises a Schwarzschild mirror objective. Preferably, the Schwarzschild mirror objective is configured to shape the laser beam without affecting the parameters of the laser beam in terms of divergence and dispersion. This makes it possible for the beam shape to acquire an annular structure with a slight transmission loss. Preferably, a Schwarzschild mirror objective has a pair of mirrors. Preferably, the Schwarzschild mirror objective is configured in such a way that, due to reflection from the pair of mirror, an annular beam can be created that converges in the object point. As a result, the optical axis behind the focus can be fundamentally kept free of primary radiation without a loss of intensity—the beam profile is preferably only re-shaped from a circular cross section to an annular cross section.

The term "intensity distribution" preferably refers to the distribution of radiation over the course of time, for example, when a pulsed laser is used, especially preferably it refers to the distribution of radiation over a surface, preferably over the cross section of the laser beam. The cross section of the laser beam is preferably a section of the laser beam at an angle of 90° relative to its direction of propagation.

Preferably, the intensity minimum is the locally smallest value of the intensity or of the radiation of the laser beam.

Preferably, the center of the cross section is the center point of the cross section. Preferably, the center point is the point that is at the same distance from all points of an imaginary circle that is arranged around the laser beam in a cross sectional plane of said laser beam. Preferably, the intensity minimum of the laser beam extends from the center of the cross section to an edge area of the laser beam, especially preferably, the intensity minimum is at a distance from an edge area of the laser beam.

Preferably, the beam-shaping device can create an annular intensity distribution in the cross section of the laser beam. By focusing and diverging a beam laser shaped in this manner, the central region of the retina and of the macula can be largely excluded from direct laser radiation. It is possible to project only an analogous annular radiation spot onto the retina.

An annular intensity distribution is preferably an intensity distribution in which the highest intensities form an annular shape. Especially preferably, an annular intensity distribution has an intensity minimum in the center of the intensity distribution. Preferably, the annular intensity distribution is a circular intensity distribution. In this context, the intensity maxima are preferably between two concentric circles having the radii $r_i$ and $r_a$. The circles with the radii $r_i$ and $r_a$ are each in an area where half of the maximum radiation is present. Especially preferably, no laser radiation is present outside of a circular ring formed by two concentric circles $r_{min}$ and $r_{max}$.

Preferably, the beam-shaping device is adjustable. This makes it possible to individually adapt the beam-shaping device to the region of the eye that is to be irradiated and to the region of the eye that is to be protected. The term adjustable preferably means that the beam-shaping device can be varied in such a way that the intensity distribution in the cross section of the laser beam can be varied. Preferably, the beam-shaping device can be adjusted two-dimensionally. Preferably, the beam-shaping device can be adjusted during the irradiation of an eye. Preferably, the beam-shaping device can be adjusted as a function of the focal position, especially preferably as a function of radiation values that have been achieved for individual regions of an eye.

Preferably, the beam-shaping device comprises a diaphragm that can be placed into an optical path in order to block off parts of the laser beam. This provides a beam-shaping device in a simple manner.

Preferably, the diaphragm comprises an opening by means of which the expansion of beam bundles can be restricted.

Preferably, an aperture diaphragm, especially preferably a safety aperture diaphragm, is employed. Preferably a fixed mechanical aperture is provided as the diaphragm. Preferably, it can be placed into the cross section of the laser beam by means of a wire holder. This makes it especially easy to shape the laser beam.

Preferably, the diaphragm is placed in the optical path in a surface or optical layer of an optical module. Preferably, an inner part of a focusing lens has a reflective coating and the edge zone is transmissively AR-coated. In this manner, an annular beam cross section can be created behind this lens without the need to insert an additional mechanical diaphragm. This avoids the need for an additional mechanical element. Preferably, the coating is done not only as a stepped profile, but with a linear or functional transition in order to commensurately take into account the aspects of safety and the requisite energy transmission.

Preferably, the diaphragm is circular or semicircular, especially preferably the diaphragm is a circular diaphragm or a pinhole. Preferably, the diaphragm is a circular plate that can be placed in the center of the laser beam by means of four wires for purposes of blocking off the center and working only with annular radiation.

Preferably, the pinhole that is inside the optical beam path of the laser system blocks off an area that is in the center of the cross section of the laser beam. Especially preferably, the pinhole only allows an outer annular area to serve as the effective radiation for focusing in the anterior segments of the eye. As a result, the regions of the eye that are irradiated by the laser can be selected in a targeted manner. Preferably, the energy or the power of the laser beam can be reduced by means of a diaphragm. As a result, the energy or the power to which the eye is exposed can be minimized. Preferably, the diaphragm is radiation-resistant. Especially preferably, the diaphragm is configured to thermally dissipate absorbed radiation energy without the occurrence of damage. Consequently, damage effects caused by high energy pulses can be avoided.

Preferably, the beam-shaping device comprises a digital micromirror device, whereby the mirrors can be varied in such a way that the irradiation of certain pre-specified regions of the eye can be minimized. This provides a beam-shaping device with which the cross section of the laser beam can be shaped in many different ways.

Preferably, a digital micromirror device (DMD) is a module that is configured to employ micromirrors in order to project an image or to reflect radiation in a targeted manner. Consequently, the laser beam can be varied in a particularly targeted manner, even in individual areas of the cross section. Moreover, the laser beam can be varied without the beam-shaping device having to be replaced. Furthermore, constant laser energy/power can be provided in that the surface area of the radiation transmitted or reflected into the eye is kept constant at the safety aperture diaphragm. In the case of a non-uniform laser beam profile, for instance, a Gaussian laser beam profile, it is possible to weight individual surface area segments and to incorporate this weighting into the calculation of the diaphragm structure for a constant laser energy/power in a therapeutic focus or target spot. Special preference is given to arranging the micromirrors in the shape of a matrix. This makes it possible to control the micromirrors in a simple manner. Preferably, as a function of the current position of the laser focal point and of the position of the regions of the eye that are not to be irradiated, the micromirrors are varied in such a way that a minimum amount of direct radiation of the laser reaches these regions. Preferably, the position of the laser focal point is prescribed by a 3D-scanner position of the laser system. This make it possible to automatically adapt the laser to the position and orientation of the eye. Preferably, the region that is not to be irradiated is the macula.

Preferably, the beam-shaping device is configured to shape the laser beam as a function of the weighting of at least two regions of the eye. This makes it possible to define regions of the eye that would be affected to different degrees by irradiation with a laser beam and to individually adapt the irradiation of the eye to this.

The term weighting preferably refers to assigning different regions of the eye to different categories, depending on how sensitive each of these regions responds to irradiation with a laser beam. Depending on the assigned category, when an eye is being irradiated and when it is unavoidable that particularly sensitive areas will also be irradiated, then a region can be selected that has been classified in a lower category. Preferably, it is also possible to take into account the radiation to which individual regions of the eye have already been exposed.

Preferably, the beam-shaping device can be positioned in a parallel optical path of the laser beam. This makes it possible to shape or structure the cross section of the laser beam in a particularly easy manner or else to shape the beam geometrically.

Preferably, the parallel optical path is an area of the laser beam where the laser radiation propagates in parallel in one direction.

Preferably, the beam-shaping device can be positioned in an intermediate image plane of the laser beam. This allows the beam-shaping device to be positioned very close to the eye. As a result, influences of the focusing device can be circumvented when the beam is shaped so that the area of the laser beam that strikes the fundus of the eye can be set very precisely.

Preferably, the intermediate image plane is an area of an intermediate image. The area of an intermediate image is preferably an area in which radiation is present that is in a state that does not correspond to the initial state or to the final state of the radiation of a device. Especially preferably, the radiation converges in the area of the intermediate image. In an intermediate image plane or conjugated plane, the diaphragm structure placed there is preferably imaged exactly into the image plane, particularly preferably into the focal plane. The image is unambiguous and preferably no optical distortion or blurring of the structure occurs.

BRIEF DESCRIPTION OF THE DRAWINGS

Preferred embodiments of the invention will be elaborated upon below, making reference to the accompanying drawings. These show the following.

DETAILED DESCRIPTION

Figure 1:
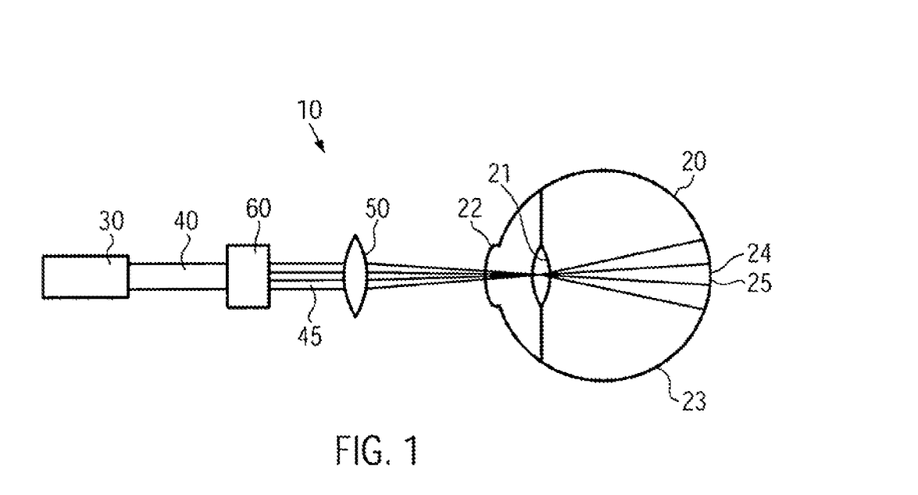
FIG. 1 a laser system according to the invention.

FIG. 1 shows a laser system 10 comprising a laser 30 that emits a continuous or pulsed laser beam 40, a pinhole 60 that is arranged in the laser beam 40, a lens 50 that is arranged in the laser beam 40 on the side of the pinhole 60 facing away from the laser, and an eye 20 that is arranged in such a way that the laser beam 40 penetrates the eye 20. In the embodiment shown here, the pinhole 60 is configured as a fixed pinhole 60. It does not change over the course of time and cannot be adapted to individual requirements of certain eyes 20. If it is necessary to shape the laser beam 40 in a different manner, the pinhole 60 is exchanged. The laser beam penetrates the eye 20 through the cornea 22, passes through the lens 21 and strikes the fundus of the eye. In this process, the laser beam 40 is focused by the lens 50 in such a way that the focus is in the lens 21. The laser beam expands again behind the lens 21.

The pinhole 60 blocks off an area that is in the center of the cross section of the laser beam 40. A laser beam having an annular cross section is formed behind the pinhole 60 in the parallel optical path 45 of the laser beam 40. As the laser beam 40 passes through the lens 50, it is focused close to the optical axis of the eye in such a way that the focus is in the lens 21. The remaining laser radiation is concentrated in one point in the focus. After the laser beam has passed through the lens 21, it expands once again so that an annular cross section is formed once again. An annular radiation spot is formed on the fundus of the eye or on the retina. This annular radiation spot is arranged in such a way that the macula 25 and the optic nerve 24 lie in the center of the radiation spot, where laser radiation is no longer present.

As a result, the optic nerve 24 and the macula 25, which are particularly sensitive places of the fundus 23 of the eye, are not exposed to the laser radiation. In this manner, it is possible to provide a high irradiation intensity in the focus of the laser beam 40, which here is in the lens 21 and, at the same time, to protect sensitive places of the fundus of the eye. Since the entire laser radiation is focused in the focus, in order to carry out measures in the anterior segment of the eye that require a certain radiation intensity, it is immaterial how the cross section of the laser beam 40 is shaped before it is focused. Since the cross section of the laser beam after the focusing also corresponds approximately to the input beam bundle, the shaping of the input laser beam 40 makes it possible to influence the radiation spot that is formed on the fundus 23 of the eye in such a way that sensitive areas of the fundus 23 of the eye are protected.

In another embodiment (not shown here), a contact lens is provided on the cornea 22. It is possible to provide other optical devices. If applicable, the pinhole 60 is adapted for this purpose.

Figure 2A:
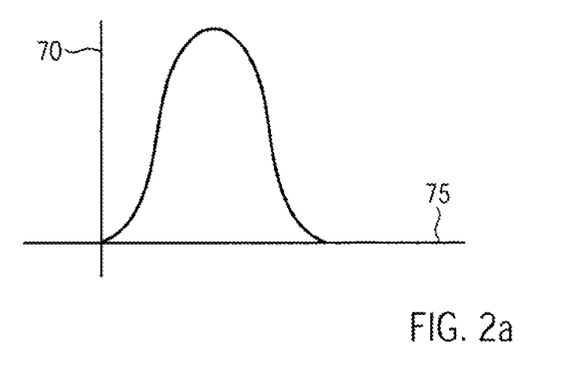
FIG. 2A a longitudinal section of a Gaussian intensity distribution in a laser beam.

FIG. 2A shows a longitudinal section of a Gaussian intensity distribution in a laser beam. The intensity or the energy flow is plotted on the vertical axis 70, while the distance from the center point of the laser beam is plotted on the horizontal axis 75. The curve is symmetrical and exhibits its maximum value in the center of the laser beam. The further away from the center point the observed area is, the lower the intensity.

Figure 2B:
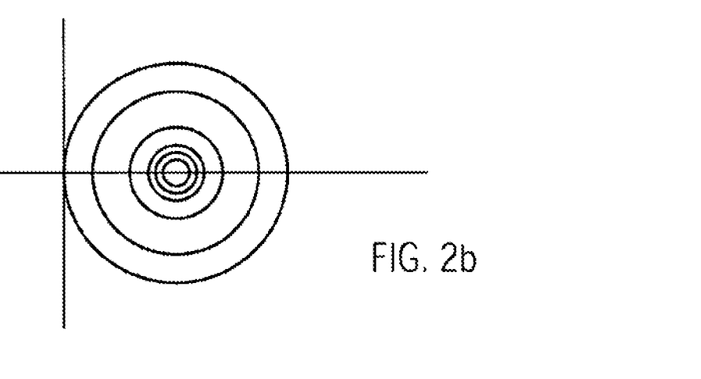
FIG. 2B a cross section of a Gaussian intensity distribution in a laser beam.

FIG. 2B shows the cross section of a Gaussian intensity distribution in a laser beam. Here, the same laser beam is used as in FIG. 2A. FIG. 2B shows concentric circles that are closer and closer together towards the center. The distance between two adjacent circles constitutes the intensity of the laser beam in the appertaining area. The laser beam exhibits its highest intensity in the center. The intensity diminishes towards the sides.

The intensity distributions in a laser beam shown in FIGS. 2A and 2B are normally employed in the state of the art for laser systems used to irradiate eyes 20. Since the laser beam does not have any areas left out where the intensity is near zero or zero, such a laser beam cannot have the effect of systematically excluding regions of the fundus of the eye from being irradiated with the laser beam 40.

Figure 3A:
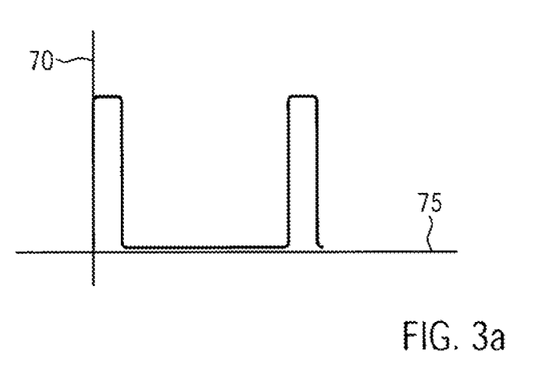
FIG. 3A a longitudinal section of an annular intensity distribution in a laser beam.

FIG. 3A shows a longitudinal section of an annular intensity distribution according to the invention in a laser beam. As was the case in FIG. 2A, the vertical axis 70 designates the intensity of the laser beam, while the horizontal axis 75 designates the distance from the center of the laser beam. The intensity of the laser beam here is highest in the outer areas of the laser beam. In the center, the intensity of the laser beam is close to zero. The curve shown has two maxima of the same magnitude.

Figure 3B:
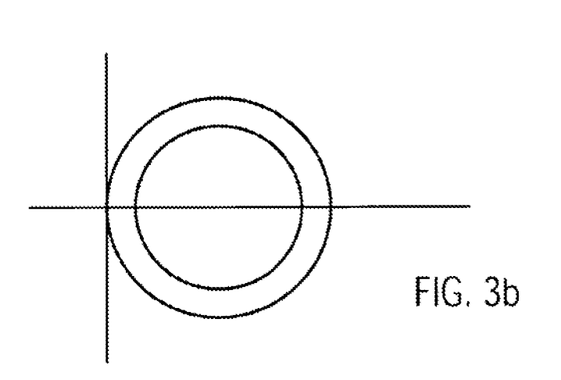
FIG. 3B a cross section of an annular intensity distribution in a laser beam.

FIG. 3B shows a cross section of an annular intensity distribution according to the invention in a laser beam. Here, the same laser beam is used as in FIG. 3A. FIG. 3B shows that the cross section of the intensity distribution is circular. In the center area, the laser radiation is near zero, whereas the intensity of the laser beam is high in the annular area that extends around the center.

With this intensity distribution according to the invention, regions of the fundus of the eye that would be irradiated when regions in the anterior segment of the eye are irradiated can be excluded from being irradiated.

Figure 4:
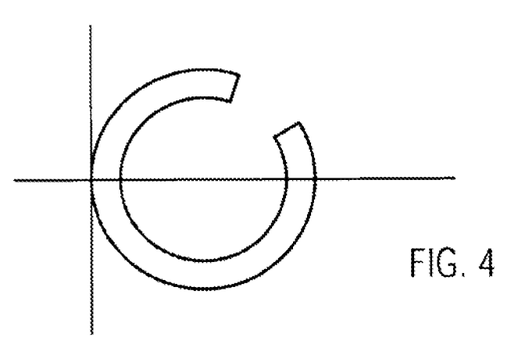
FIG. 4 a cross section of another intensity distribution in a laser beam.

FIG. 4 shows a cross section of another intensity distribution in a laser beam. The intensity distribution shown in FIG. 4 corresponds to the intensity distribution shown in FIG. 3B, except that the circular ring is not complete. The circular ring extends along about 300° of the circumference.

Consequently, regions of the fundus of the eye that would be irradiated in the case of a complete circular ring can also be excluded from being irradiated.

Figure 5:
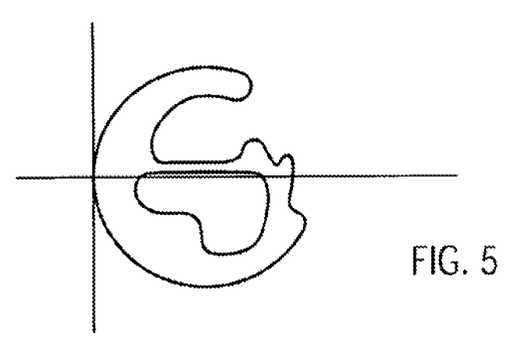
FIG. 5 a cross section of another intensity distribution in a laser beam.

FIG. 5 shows an irregular free-form surface that likewise has an irregular area left out.

Since the cross section of the laser beam can be shaped at will, any desired regions of the fundus 23 of the eye can be excluded from being irradiated.

List of Reference Numerals

10 laser system
20 eye
21 lens
22 cornea
23 fundus of the eye
24 optic nerve
25 macula
30 laser
40 laser beam/pulsed ultraviolet laser beam
45 parallel optical path
50 focusing device/lens
60 beam-shaping device/pinhole
70 vertical axis
75 horizontal axis

The invention claimed is:

1. A laser system for the irradiation of an eye comprises:
a laser configured to emit a laser beam;
a focusing device configured to focus the laser beam in a vicinity of a lens of the eye so as to treat the eye; and
a beam-shaping device configured to generate a predetermined intensity distribution in a cross section of the laser beam such that an intensity minimum of the laser beam is disposed in a region of center of the cross section of the laser beam,
wherein the beam-shaping device is configured to shape the laser beam as a function of a weighing of at least two regions of the eye.

2. The laser system as recited in claim 1, wherein the predetermined intensity distribution is annular.

3. The laser system as recited in claim 1, wherein the beam-shaping device is adjustable for changing the predetermined intensity distribution.

4. The laser system as recited in claim 1, wherein the beam shaping device includes a diaphragm configured to be disposed into an optical path so as to block parts of the laser beam.

5. The laser system as recited in claim 1, wherein the beam shaping device includes a digital micromirror device having a plurality of micromirrors, wherein the plurality of micromirrors are variable so as to minimize an irradiation from the laser beam of certain pre-specified regions of the eye.

6. The laser system as recited in claim 1, wherein the beam-shaping device can be positioned in an optical path parallel to the laser beam.

7. The laser system as recited in claim 1, wherein the beam-shaping device can be positioned in an intermediate image plane of the laser beam.

8. The laser system as recited in claim 1, wherein the focus of the laser beam has a diameter in a range of 1 μm to 20 μm.

9. A method for treating an eye comprising:
emitting a laser beam using a laser;
focusing the laser beam in a vicinity of a lens of the eye using a focusing device so as to treat the eye; and
generating a predetermined intensity distribution in a cross section of the laser beam using a beam-shaping device such that an intensity minimum of the laser beam is disposed in a region of a center of the cross section of the laser beam,
wherein the beam-shaping device shapes the laser beam as a function of a weighting of at least two regions of the eye.

10. The method recited in claim 9, wherein the focus of the laser beam has a diameter in a range of 1 μm to 20 μm.

* * * * *